United States Patent [19]

Matsuura

[11] Patent Number: 5,050,584
[45] Date of Patent: Sep. 24, 1991

[54] ENDOSCOPE WITH A SOLID-STATE IMAGE PICKUP DEVICE

[75] Inventor: Nobuyuki Matsuura, Hino, Japan

[73] Assignee: Olympus Optical Co., Ltd., Tokyo, Japan

[21] Appl. No.: 557,560

[22] Filed: Jul. 24, 1990

[30] Foreign Application Priority Data

Sep. 22, 1989 [JP] Japan .................................. 1-247492
Apr. 20, 1990 [JP] Japan .................................. 2-104913

[51] Int. Cl.$^5$ .............................................. A61B 1/00
[52] U.S. Cl. ......................................... 128/4; 128/6; 358/98
[58] Field of Search ........................ 128/4, 6; 358/98

[56] References Cited

U.S. PATENT DOCUMENTS

| 4,491,865 | 1/1985 | Danna et al. | 358/98 |
| 4,779,130 | 10/1988 | Yabe | 358/98 |
| 4,918,521 | 4/1990 | Yabe et al. | 358/98 |

FOREIGN PATENT DOCUMENTS 62-31820 2/1987 Japan .

Primary Examiner—William H. Grieb
Attorney, Agent, or Firm—Kenyon & Kenyon

[57] ABSTRACT

An endoscope having a distal end portion including an objective lens system and a solid-state image pickup device. An optical member having a diameter larger than that of the objective lens system is arranged between the objective lens system and the solid-state image pickup device. Only the objective lens system is supported by a supporting frame. Thus, the diameter of the distal end portion of the endoscope can be reduced.

9 Claims, 6 Drawing Sheets

ENDOSCOPE WITH A SOLID-STATE IMAGE PICKUP DEVICE

BACKGROUND OF THE INVENTION

1. Field of the Invention

This invention relates to an endoscope provided with an objective lens and a solid-state image pickup device in its distal end portion.

2. Description of the Related Art

In recent years, wide use has been made of endoscopes which have elongated inserting portions to be inserted into body cavities to make a diagnosis or test of internal organs. Also in the industrial or technical field, endoscopes are used to observe and examine the interior of a boiler, machine, chemical plant, or the like.

Furthermore, use has been made of various electronic endoscopes which have solid-state image pickup devices, such as CCDs. The solid-state image pickup device is arranged at the distal end of the inserting portion of an endoscope to be inserted into an examined part, for example, a body cavity. A means for mounting the solid-state image pickup device and an objective lens system for imaging an object on the solid-state image pickup device (hereinafter called "imaging system") is disclosed in, for example, Japanese Laid-Open Patent Application, Publication No. 62-31820. However, as the application fields of endoscopes have been diversified, it is desired to compact the imaging system to reduce the diameter of the distal end portion.

Thus, an imaging system as shown in FIG. 10 has been proposed. A concave objective lens 78a, convex objective lenses 78b and 78c, and a solid-state image pickup device 82 are arranged and supported in a substantially cylindrical supporting frame 77. The rear surface of the objective lens 78c is contacted by cementing or the like to a mask 81 for preventing the diffused reflection from the solid-state image pickup device 82, and an epoxy resin layer of the solid-state image pickup device 82.

In the above imaging system, however, since the objective lens 78c is contacted to the solid-state image pickup device 82, it is necessary to make the diameter of the objective lenses 78a to 78c large enough to utilize the imaging surface of the solid-state image pickup device 82. Furthermore, the supporting frame 77 should be thick because it also supports the solid-state image pickup device 82. Consequently, there is a problem that the distal end portion becomes thick.

U.S. Pat. No. 4,491,865 discloses an image sensor assembly in which a lens system is supported by a lens barrel which, in turn, is arranged in the front of a cylindrical housing, a solid state image sensor is arranged in the back of the housing, and a gas tight chamber is formed between the lens system and the image sensor. However, this structure requires the cylindrical housing for supporting the lens barrel and the solid state image sensor, thus the distal end becomes thick. There is also a problem that the assembly is elongated in the direction of the optical axis since the gas tight chamber is provided.

SUMMARY OF THE INVENTION

It is therefore an object of the present invention to reduce the diameter of the imaging system to provide an endoscope having a thin distal end portion.

Another object of the invention is to reduce the diameter of the distal end portion of an endoscope to mitigate pain of a patient when the endoscope is inserted into the patient.

These and other objects of the present invention are attained by an endoscope having a distal end portion in which between an objective lens system and a solid-state image pickup device is arranged an optical member having a diameter larger than that of the objective lens system, and only the objective lens system is supported by a supporting frame without requiring any supporting frame for the solid-state image pickup device. Thus, the distal end portion of the endoscope can be reduced.

Furthermore, the objective lens system is designed in such a manner that among the effective rays incident on the solid-state image pickup device, the ray imaged at the farthest position from the optical axis of the objective lens system increasingly goes away from the optical axis as the ray approaches the solid-state image pickup device. Thus, the diameter of the objective lens system can be small and the distal end portion of the endoscope can be thin.

DESCRIPTION OF THE PREFERRED EMBODIMENTS

Figure 1:
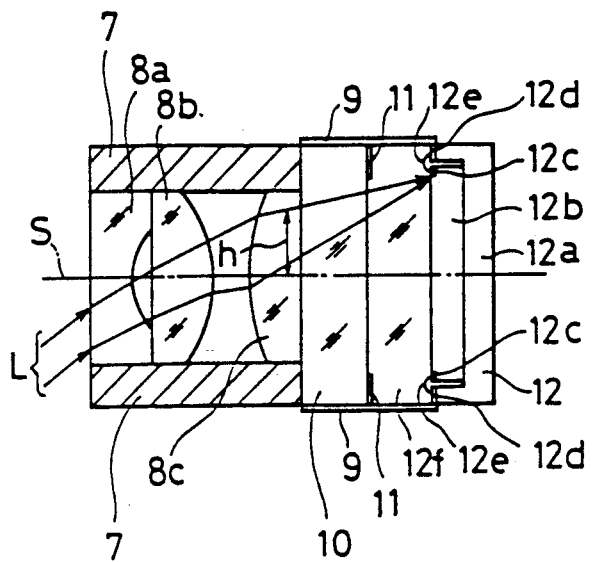
FIG. 1 is a sectional view of an objective lens system and a solid-state image pickup device according to a first embodiment of the present invention.

Referring to the drawings, embodiments of the present invention will be described.

Figure 2:
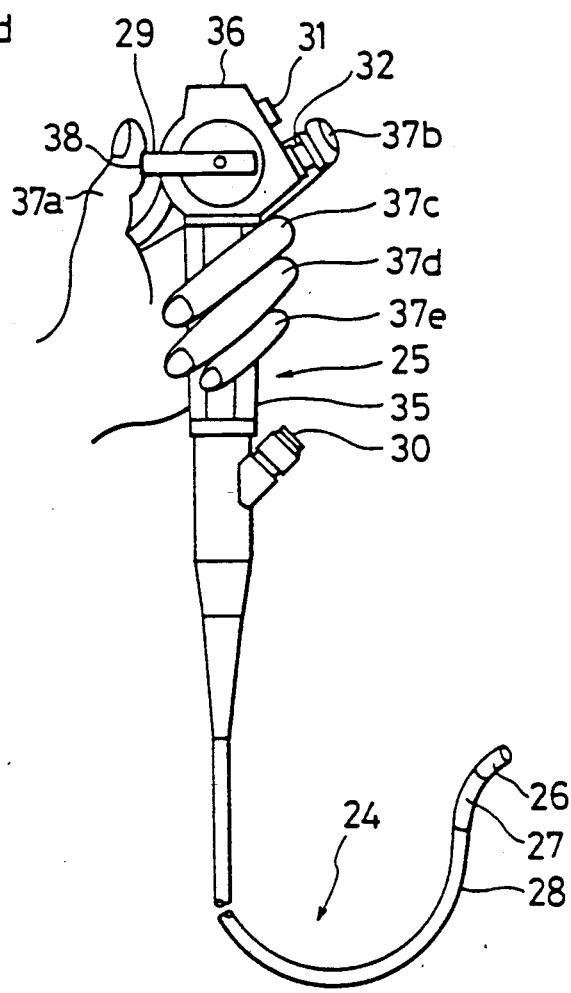
FIG. 2 is an outside view of an electronic endoscope according to the first embodiment.
Figure 3:
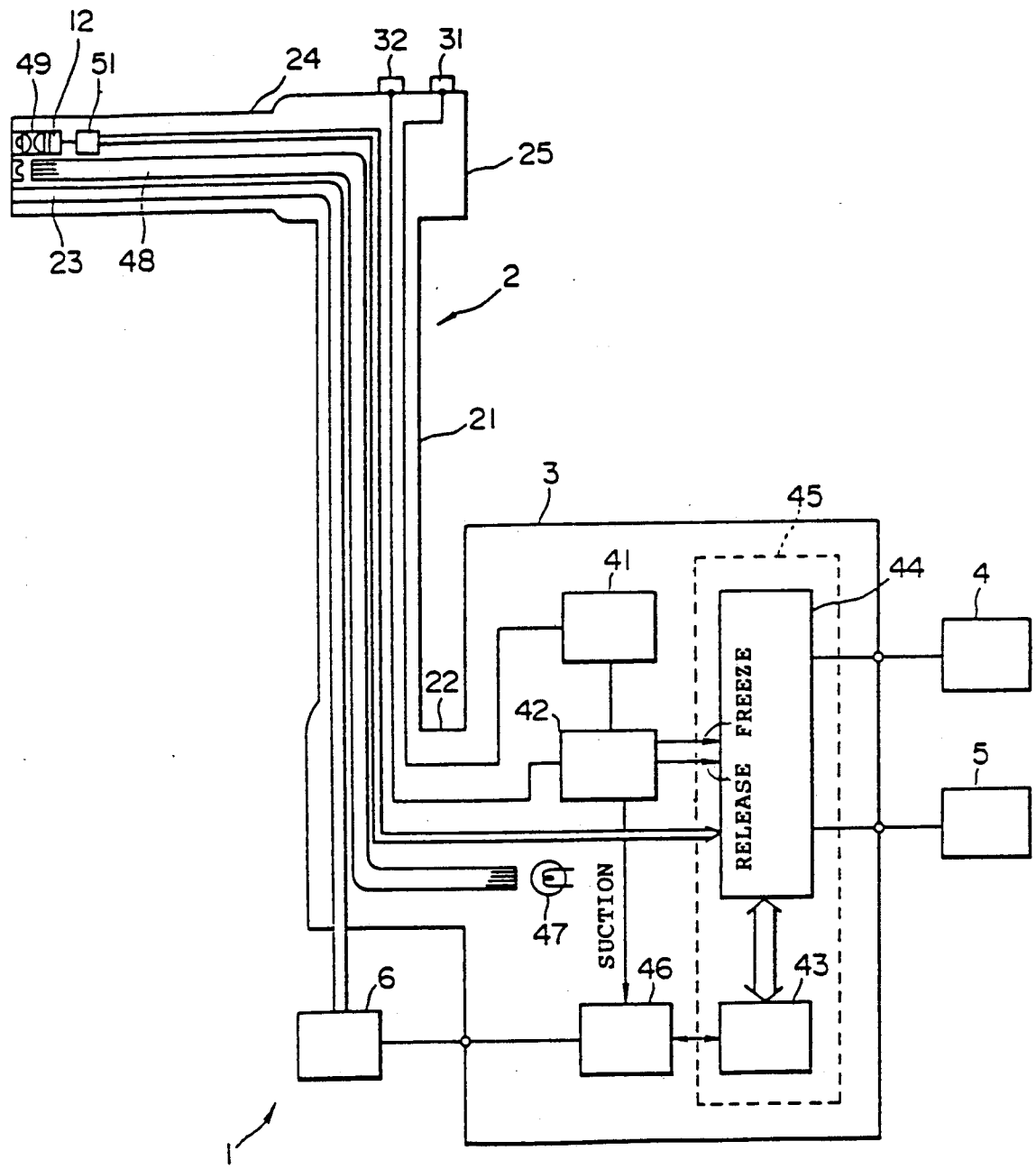
FIG. 3 is a block diagram illustrating an endoscope system according to the first embodiment.

FIGS. 1 to 3 relate to a first embodiment of the present invention. FIG. 1 is a sectional view of an objective lens system and a solid-state image pickup device, FIG. 2 is an outside view of an electronic endoscope, and FIG. 3 is a schematic diagram of an endoscope system.

An endoscope system 1 shown in FIG. 3 comprises an endoscope 2 having an elongated form to be inserted into, for example, a body cavity; a control unit 3 to which a universal cord 21 of the endoscope 2 is connected via a connector 22; a monitor apparatus 4 for displaying an image of an object (not shown), such as a body cavity, on the basis of an output signal of the control unit 3; a recording apparatus 5, such as a magnetic recording apparatus of the disk cartridge type and a photographing apparatus, for recording an image of an object (not shown), such as a body cavity, on the basis of an output signal of the control unit 3; and a suction apparatus 6 responsive to a signal of the control unit 3 for sucking body fluid or blood out of an body cavity through a suction tube 23 passing through the endoscope 2 and connected to the suction apparatus 6 via the connector 22.

As shown in FIG. 2, the endoscope 2 has an elongated flexible inserting portion 24 to be inserted into, for example, a body cavity, and an operating portion 25 provided on the proximal side of the inserting portion 24. The inserting portion 24 comprises, from the proximal side, a long flexible tube portion 28, a bending portion 27, and a distal end portion 26. The operating portion 25 is provided with a substantially columnar grasping portion 35 on the side of the inserting portion 24, and a switch portion 36 on the proximal side of the grasping portion 35. One side of the switch portion 36 is formed as a slanting surface going away from the longitudinal axis of the grasping portion 35 as it approaches the inserting portion 24. On the slanting surface, a first operating button 31 is provided at a position far from the grasping portion 35, and a second operating button 32 is arranged at a position nearer to the grasping portion 35. Further, on a side adjacent to the slanting surface, an angle lever 29 is provided. The angle lever 29 is L-shaped, its one end is rotatably supported, and a thumb applying portion 38 is provided at the other end. When the angle lever 29 is operated, the bending portion 27 is bent, for example, right and left, or up and down. An operator grasps the grasping portion 25 by his middle finger 37c, ring finger 37d, and little finger 37e and operates the first and second operating buttons 31 and 32 with his forefinger 37b and the thumb applying portion 38 of the angle lever 29 with his thumb 37a.

The operating portion 25 is also provided with a forceps inlet 30 for inserting an treating instrument or the like through a channel (not shown) communicating with the distal end portion 26.

As shown in FIG. 3, the control unit 3 comprises a control circuit 41 to which a signal line coming from the first operating button 31 through the universal cord 21 is connected via the connector 22; a selector 42 to which a signal line coming from the second operating button through the universal cord 21 is connected via the connector 22; a video circuit 45 comprising a central processing unit 43 and an input/output (I/O) circuit 44 for the signal processing of image signals and the control of various accessory apparatus; a suction control circuit 46 for controlling the suction apparatus 6 in response to a signal of the second operating button 32 changed over by the selector 42; and a light source lamp 47 for supplying illumination light to the endoscope 2.

A light guide 48 for transmitting the illumination light passes through the endoscope 2. The illumination light is supplied to the light entering end of the light guide 48 from the light source lamp 47 in the control unit 3, transmitted to the light emitting end in the distal end portion 26 and emitted to an object (not shown) from the light emitting end.

The distal end portion 26 is provided with an objective lens system 49, and an solid-state image pickup device 12 is arranged at the imaging position of the objective lens system 49. The object is imaged on the image pickup surface of the solid-state image pickup device 12, and the image is transduced to an image signal. The solid-state image pickup device 12 is connected to a common mode rejection amplifier (hereinafter called "CMR amplifier") 51 which has a large capability for rejecting the common mode noise of an electric signal and amplifies the image signal transduced by the solid-state image pickup device 12. The CMR amplifier 51 is connected to a signal line and a dummy line for rejecting the noise, and the signal line and the dummy line pass through the universal cord 21 and are connected to the I/O circuit 44 of the control unit 3. The image signal undergoes various signal processings by the I/O circuit 44 and becomes a video signal to be outputted to the monitor apparatus 4 and the recording apparatus 5.

The recording apparatus 5 records the picked-up image on a magnetic medium, such as a disk cartridge, in response to a release signal from the I/O circuit 44.

When the first operating button 31 is operated, the control circuit 41 causes the selector 42 to change over the signal line of the second operating button 32 to a freeze signal input terminal and a release signal input terminal of the I/O circuit 44, and a control terminal of the suction control circuit 46. The apparatus actuated or operation performed by operating the second operating button 32 is displayed on the monitor apparatus 4.

Thus, if the first operating button 31 has been operated to cause the signal line of the second operating button 32 to be connected to the freeze signal input terminal of the I/O circuit 44, the operation of the second operating button 32 will cause the I/O circuit 44 to freeze the image displayed on the monitor apparatus 4. If the first operating button 31 has been operated to cause the signal line of the second operating button 32 to be connected to the release signal input terminal of the I/O circuit 44, the operation of the second operating button 32 will cause the I/O circuit 44 to record on the recording medium, such as a disk cartridge, the image displayed on the monitor apparatus 4. Further, if the first operating button 31 has been operated to cause the signal line of the second operating button 32 to be connected to the control terminal of the suction control circuit 46, the operation of the second operating button 32 will cause the suction apparatus 6 to suck body fluid or the like out of the body cavity in response to a signal from the suction control circuit 46. The recording apparatus 5 may be an optical information recording apparatus using an optical disk or the like as a recording medium, or a still camera using film as a recording medium.

As shown in FIG. 1, the objective lens system 1 comprises a lens frame 7 which is substantially cylindrical and does not transmit light; a concave objective lens 8a arranged in the lens frame 7 and having a substantially plane surface on which the light from the object impinges; a convex objective lens 8b having a substantially plane surface adjacent to the objective lens 8a; and a convex objective lens 8c having a substantially plane surface adjacent to the below-mentioned optical member 10.

The solid-state image pickup device 12 comprises a substantially columnar base 12a; a chip 12b mounted on the base 12a; circuit line ends 12c provided on the fringe of the image pickup surface of the chip 12b; lands 12d provided on the base 12a in the vicinity of the chip 12b and opposite to the circuit line ends 12c; wires 12e for electrically connecting the circuit line ends 12c and the lands 12d; and a transparent epoxy resin layer 12f arranged in front of the image pickup surface of the chip 12b.

The epoxy resin layer 12f is provided with a mask 11 functioning as a flare stop on the fringe of its surface remote from the chip 12b.

An optical member 10 is provided by bonding or the like between and in contact with the objective lens system 49 and the epoxy resin layer 12f of the solid-state image pickup device 12. The optical member 10 is transparent and substantially columnar and has substantially the same outer diameter as that of the lens frame 7 of the objective lens system 49.

The optical member 10 and the epoxy resin layer 12f are provided on their peripheries with a shading member 9 for preventing the light other than that transmitted through the objective lenses 8a to 8c from impinging on the solid-state image pickup device 12.

Among the effective rays incident on the solid-state image pickup device, the pencil of rays which are imaged at the farthest position from the optical axis is represented by the letter L. The height h of the pencil of rays L from the object with respect to the optical axis S increases as the pencil of rays approaches the image pickup surface of the chip 12b of the solid-state image pickup device 12. The height of the pencil of rays entering the objective lens 8a with respect the optical axis S is substantially the same as that of the pencil of rays emerging from the objective lens 8c with respect to the optical axis S.

Thus, the outer diameter of the objective lenses 8a to 8c and the lens frame 7 holding the objective lenses 8a to 8c can be reduced by providing the optical member 10 between the objective lens system 49 and the solid-state image pickup device 12, as described above.

Figure 4:
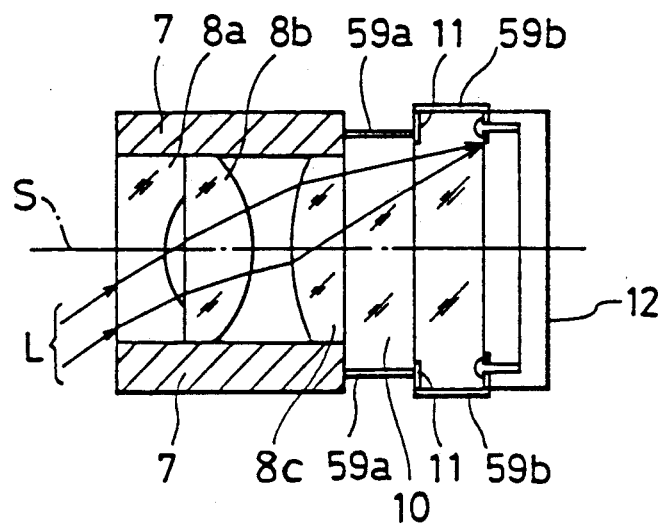
FIG. 4 is a sectional view of an objective lens system and a solid-state image pickup device according to a second embodiment of the present invention.

FIG. 4 is a sectional view of an objective lens and a solid-state image pickup device according to a second embodiment of the present invention. The same elements as those of the first embodiment are assigned the same symbols and their description is omitted. Further, the endoscope and the endoscope system are the same as in the first embodiment and their description is not repeated.

In this embodiment, a substantially plane surface of an objective lens 8c contacts by bonding or the like to a substantially columnar optical member 10 whose outer diameter is larger than that of the objective lens 8c and smaller than that of a lens frame 7. The other end surface of the optical member 10 contacts by bonding or the like to a solid-state image pickup device 12 provided with a mask 11.

The optical member 10 and an epoxy resin layer of the solid-state image pickup device 12 are provided on their peripheries with shading members 59a and 59b, respectively.

The function and effect of the objective lens system and the solid-state image pickup device so constructed are the same as in the first embodiment.

Figure 5:
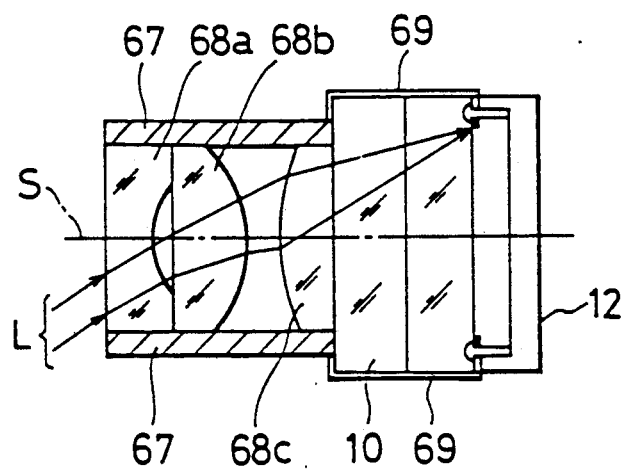
FIG. 5 is a sectional view of an objective lens system and a solid-state image pickup device according to a third embodiment of the present invention.

FIG. 5 is a sectional view of an objective lens and a solid-state image pickup device according to a third embodiment of the present invention. The same elements as those of the first and second embodiment are assigned the same symbols and their description is omitted. Further, the endoscope and the endoscope system are the same as in the first embodiment and their description is not repeated.

The objective lens system of this embodiment comprises a lens frame 67 which is substantially cylindrical and does not transmit light; a concave objective lens 68a arranged in the lens frame 67 and having a substantially plane surface on which the light from the object impinges; a convex objective lens 68b having a substantially plane surface adjacent to the objective lens 68a; and a convex objective lens 68c having a substantially plane surface adjacent to the below-mentioned optical member 10.

The substantially plane surface of the objective lens 68c contacts by bonding or the like to a substantially columnar optical member 10 whose outer diameter is larger than that of the lens frame 67. The other end surface of the optical member 10 contacts by bonding or the like to a solid-state image pickup device 12.

A shading member 69 is provided on the peripheries of the optical member 10 and an epoxy resin layer of the solid-state image pickup device 12, and on the fringe of the front surface of the optical member 10 between the lens frame 67 and the periphery of the optical member 10.

With this structure, the pencil of light L from the object impinges slantingly on the image pickup surface of the solid-state image pickup device 12.

The effect of this embodiment is the same as in the first and second embodiments.

In the above embodiments, the shading member may be a coating of shading material.

Figure 7:
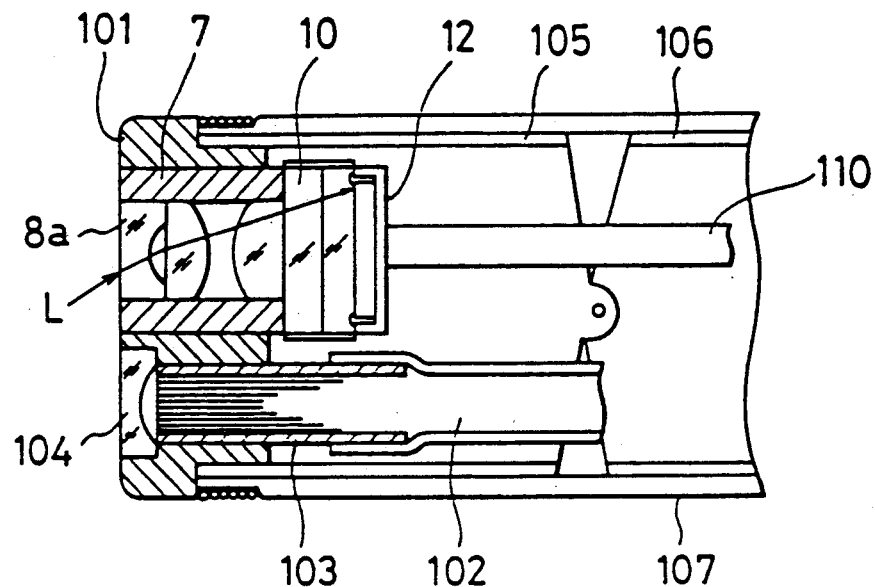
FIG. 7 is a sectional view showing an example of the distal end position of an endoscope provided with the objective lens system and the solid-state image pickup device of the first embodiment.

FIG. 7 shows an example of the distal end portion of an endoscope provided with the objective lens system and the solid-state image pickup device of the first embodiment. A distal end member 101 is provided with the objective lens system of the first embodiment and the distal end of a light guide 102. As described above, the solid-state image pickup device 12 is positioned behind the objective lens system via the optical member 10. The solid-state image pickup device 12 is connected with a cable 110 for transmitting electric signals. The light guide 102 is provided at its distal end with a metallic tube 103, in front of which an illuminating lens 104 is mounted. Behind the distal end member 101, there are provided a first articulation ring 105 and subsequent articulation rings 106 to form a bending portion 107. In this example, since the lens frame 7 does not extend to the periphery of the solid-state image pickup device 12, it is possible to spare space and reduce the diameter of the distal end portion. In the figure, L represents a ray.

Figure 8:
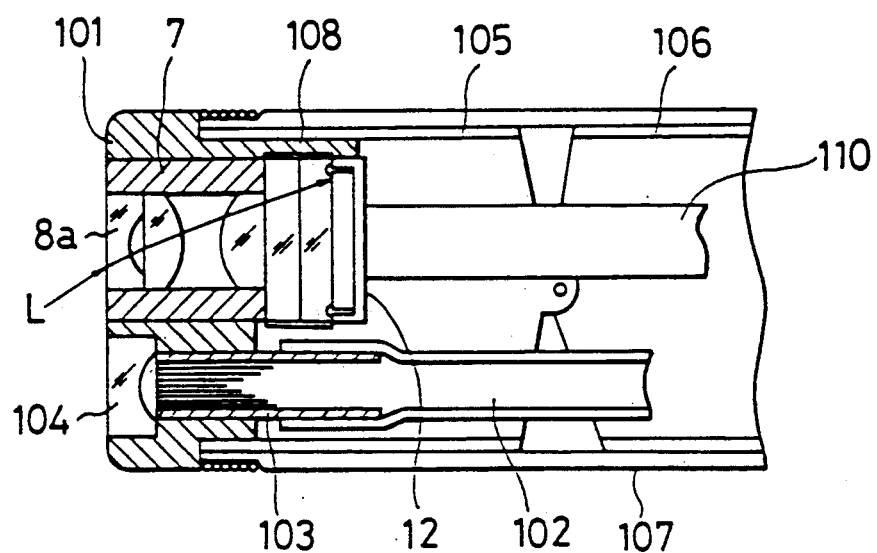
FIG. 8 is a sectional view showing another example of the distal end position of an endoscope provided with the objective lens system and the solid-state image pickup device of the first embodiment.

FIG. 8 shows another example of the distal end portion of an endoscope provided with the objective lens system and the solid-state image pickup device of the first embodiment. This example is different from that shown in FIG. 7 in that a part of the rear end of a distal end member 101 extends to the periphery of the solid-state image pickup device 12 to from an extending portion 108 so as to reinforce the fixing of the objective lens system, the optical member 10 and the solid-state image pickup device 12.

Figure 9:
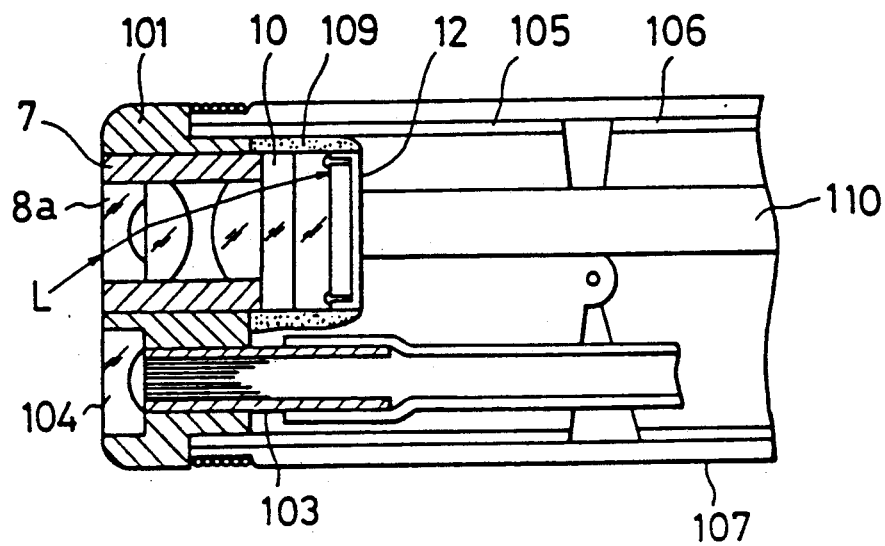
FIG. 9 is a sectional view showing still another example of the distal end position of an endoscope provided with the objective lens system and the solid-state image pickup device of the first embodiment.
Figure 10:
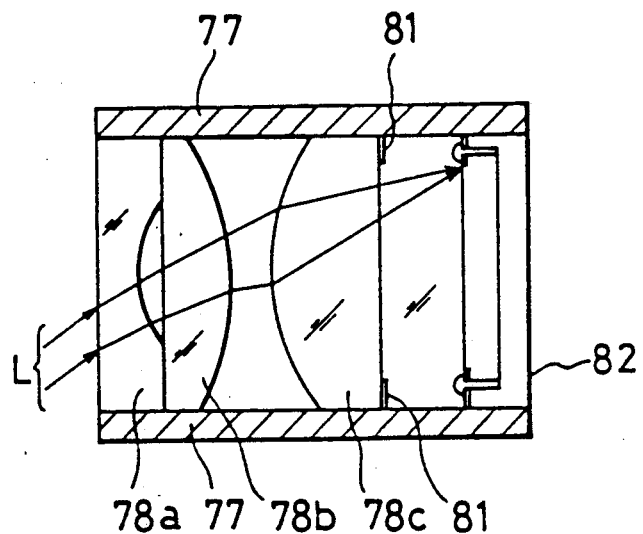
FIG. 10 is a sectional view of an objective lens system and a solid-state image pickup device in a conventional imaging system.

FIG. 9 shows still another example of the distal end portion of an endoscope provided with the objective lens system and the solid-state image pickup device of the first embodiment, except that the shading member 9 in the first embodiment is not used. In this example, the peripheries of the optical member 10 and the solid-state image pickup device 12 are sealed by an opaque sealing member 109 to reinforce the fixing.

Additionally, the operating portion of an endoscope is provided with a plurality of operating buttons as the function of the endoscope system has been diversified. However, it is difficult to make the grasping portion of the endoscope very thick because it must be surely grasped by the fingers.

Figure 6:
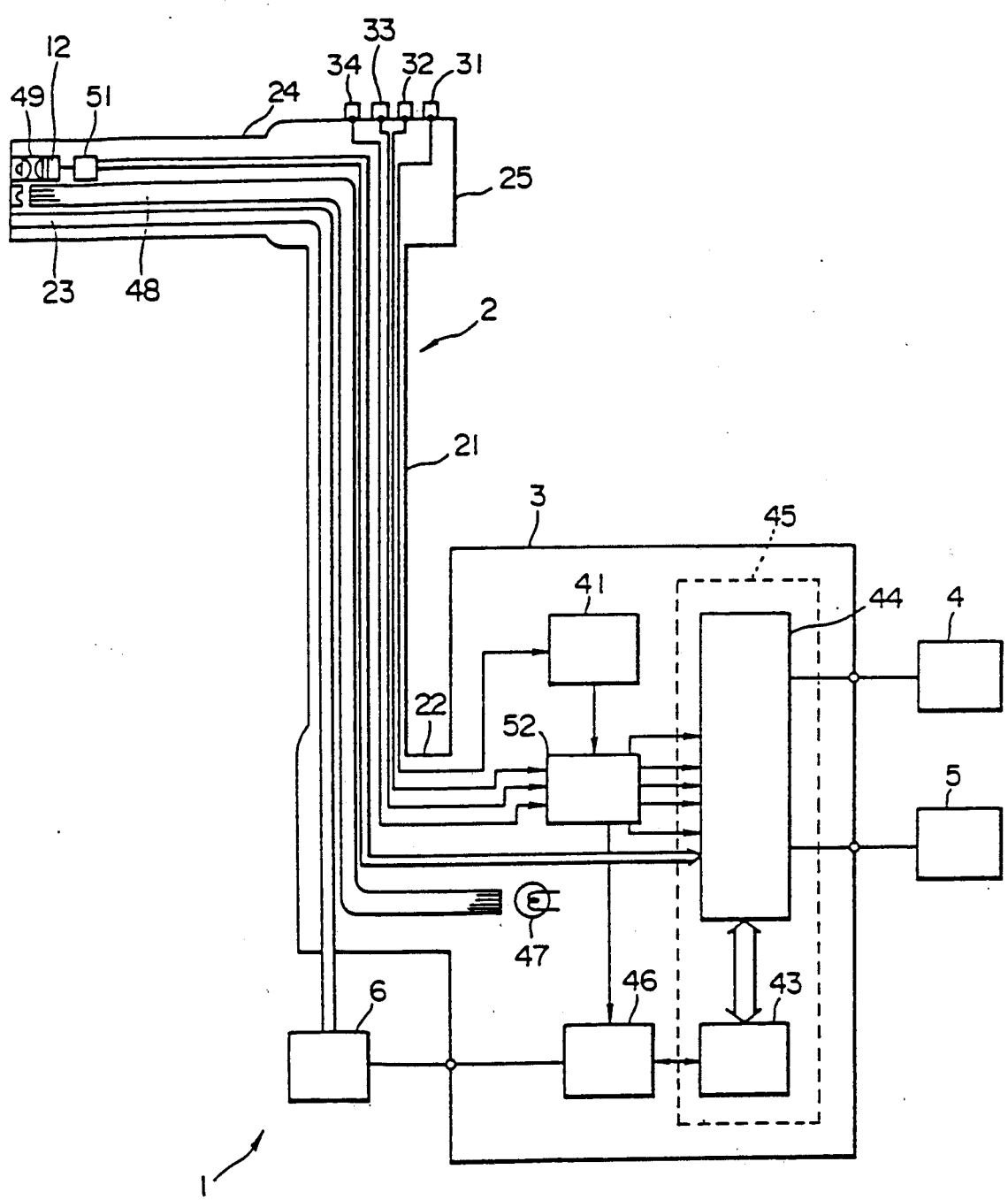
FIG. 6 is a block diagram illustrating another endoscope system according to the present invention.

Therefore, as shown in FIG. 6, a first operating button 31 provided on an operating portion 25 is connected to a control circuit 41, and the control output terminal of the control circuit 41 is connected to a selector 52. The selector 52 is connected to a second, third and fourth operating buttons 32, 33 and 34, and the output terminals of the selector 52 are connected to, for example, a suction control circuit 46 and an I/O circuit 44. The other structure is the same as in the first embodiment: the same members are assigned the same numerals and their description is omitted.

The output terminals of the selector 52 can perform two operations for each of the second, third and fourth operating buttons 32, 33 and 34 by the actuation of the first operating button 31. For example, the second operating button 32 can be used for suction control and freeze, the third operating button 33 for the control of air and water supply, and the fourth operating button 34 for release and the start/stop control of a VTR apparatus (not shown). The control mode of each operating button is displayed on, for example, a monitor apparatus 4.

Thus, six kinds of control can be made by the four operating buttons provided on the operating portion 25 to improve the operation of the endoscope. The operating buttons may also control other apparatus, for example, peripheral apparatus, and the number of operating buttons is not limited to that disclosed herein.

What is claimed is:

1. An endoscope having a distal end portion, the distal end portion comprising:
   an objective lens system comprising a plurality of lenses and having an optical axis and a diameter;
   a supporting frame for supporting the objective lens system;
   a first optical member fixed behind the supporting frame to the objective lens system and having a diameter larger than that of the objective lens system; and
   a solid-state image pickup device fixed behind the first optical member;
   the objective lens system being designed in such a manner that among the effective rays incident on the solid-state image pickup device, the ray imaged at the farthest position from the optical axis of the objective lens system increasingly goes away from the optical axis as the ray approaches the solid-state image pickup device and that the distance between the ray at the image plane of the solid-state image pickup device and the optical axis is larger than the radius of the objective lens system.

2. The endoscope of claim 1, wherein the solid-state image pickup device comprises a base, a chip mounted on the base, and a second optical member for covering the chip, the second optical member having a front surface, and the first optical member is fixed to the front surface of the second optical member.

3. The endoscope of claim 2, wherein the first and second optical members have side surfaces covered by a shading member.

4. The endoscope of claim 2, wherein the first optical member is formed by an epoxy resin layer.

5. The endoscope of claim 2, wherein the second optical member is provided on the fringe of the front surface with a mask functioning as a flare stop.

6. The endoscope of claim 1, wherein the supporting frame has an outer diameter which is substantially the same as the diameter of the first optical member.

7. The endoscope of claim 1, wherein the supporting frame has an outer diameter which is larger than the diameter of the first optical member.

8. The endoscope of claim 1, wherein the supporting frame has an outer diameter which is smaller than the diameter of the first optical member.

9. The endoscope of claim 1, wherein the lens positioned in the rear of the supporting frame has a plane rear surface which is level with the rear of the supporting frame and cemented to the first optical member.

* * * * *